United States Patent
Clark et al.

(10) Patent No.: US 10,687,155 B1
(45) Date of Patent: Jun. 16, 2020

(54) SYSTEMS AND METHODS FOR PROVIDING PERSONALIZED AUDIO REPLAY ON A PLURALITY OF CONSUMER DEVICES

(71) Applicant: Mimi Hearing Technologies GmbH, Berlin (DE)

(72) Inventors: Nicholas R. Clark, Royston (GB); Michael Hirsch, Berlin (DE)

(73) Assignee: Mimi Hearing Technologies GmbH, Berlin (DE)

(*) Notice: Subject to any disclaimer, the term of this patent is extended or adjusted under 35 U.S.C. 154(b) by 0 days.

(21) Appl. No.: 16/540,345

(22) Filed: Aug. 14, 2019

(51) Int. Cl.
*H04R 25/00* (2006.01)

(52) U.S. Cl.
CPC ......... *H04R 25/505* (2013.01); *H04R 25/305* (2013.01); *H04R 25/70* (2013.01)

(58) Field of Classification Search
CPC ...... H04R 25/50; H04R 25/505; H04R 25/70; H04R 2225/55
See application file for complete search history.

(56) References Cited

U.S. PATENT DOCUMENTS

| | | | | |
|---|---|---|---|---|
| 6,840,908 B2* | 1/2005 | Edwards | ............... | A61B 5/121 600/559 |
| 8,538,033 B2* | 9/2013 | Wilson | ................ | A61B 5/12 381/60 |
| 8,548,179 B2* | 10/2013 | Nishizaki | ............... | A61B 5/121 381/312 |
| 8,917,892 B2* | 12/2014 | Poe | ....................... | H04R 25/70 381/312 |
| 8,948,427 B2* | 2/2015 | Wessel | ................... | H04R 25/70 381/314 |
| 9,344,815 B2* | 5/2016 | Selig | ....................... | H04R 25/50 |
| 9,344,817 B2* | 5/2016 | Eaton | .................... | H04R 25/554 |
| 9,516,438 B2* | 12/2016 | Andersen | .............. | H04R 25/70 |
| 9,641,943 B2* | 5/2017 | Sabin | ...................... | H04R 25/50 |
| 9,832,562 B2* | 11/2017 | De Vries | .............. | H04R 25/505 |
| 10,187,733 B2* | 1/2019 | Schneider | ............. | H04R 25/55 |
| 10,199,047 B1 | 2/2019 | Clark | | |
| 10,398,360 B1 | 9/2019 | Clark | | |
| 10,455,335 B1 | 10/2019 | Clark | | |
| 2010/0080398 A1* | 4/2010 | Waldmann | .......... | H04R 25/658 381/66 |

(Continued)

OTHER PUBLICATIONS

Anwar et al.; "Data mining of audiology patient records: factors influencing the choice of hearing aid type"; Apr. 30, 2012; BMC medical informatics and decision making; vol. 12 Suppl 1,Suppl 1 S6 (Year: 2012).*

*Primary Examiner* — Fan S Tsang
*Assistant Examiner* — Ryan Robinson
(74) *Attorney, Agent, or Firm* — Polsinelli PC

(57) ABSTRACT

Systems and methods for processing an audio signal are provided for server-mediated sound personalization on a plurality of consumer devices. A user hearing test is conducted on one of a plurality of audio output devices. Next, the hearing data of the user's hearing test is outputted to a server and stored on the server's database along with a unique user identifier. Next, a set of DSP parameters for a sound personalization algorithm are calculated from the user's hearing data. The DSP parameter set is then outputted to one of a plurality of audio output devices when the user logs in with their unique identifier on an application on the audio output device.

20 Claims, 16 Drawing Sheets

(56) References Cited

U.S. PATENT DOCUMENTS

| | | | |
|---|---|---|---|
| 2014/0194775 A1* | 7/2014 | Van Hasselt | A61B 5/123 600/559 |
| 2015/0146876 A1* | 5/2015 | Nishizaki | H04R 25/70 381/60 |
| 2016/0135719 A1* | 5/2016 | von Kraus | A61B 90/361 600/559 |
| 2017/0257713 A1* | 9/2017 | Westermann | G06F 19/3418 |
| 2018/0063653 A1* | 3/2018 | Aschoff | H04R 25/505 |
| 2018/0132046 A1* | 5/2018 | Westermann | H04R 25/558 |
| 2018/0270590 A1* | 9/2018 | Rountree, Sr. | H04R 25/70 |
| 2018/0296137 A1* | 10/2018 | Anderson | A61B 5/4836 |
| 2019/0231232 A1* | 8/2019 | Clark | A61B 5/121 |
| 2019/0320268 A1* | 10/2019 | Blau | A61B 5/743 |
| 2019/0392849 A1 | 12/2019 | Clark | |

\* cited by examiner

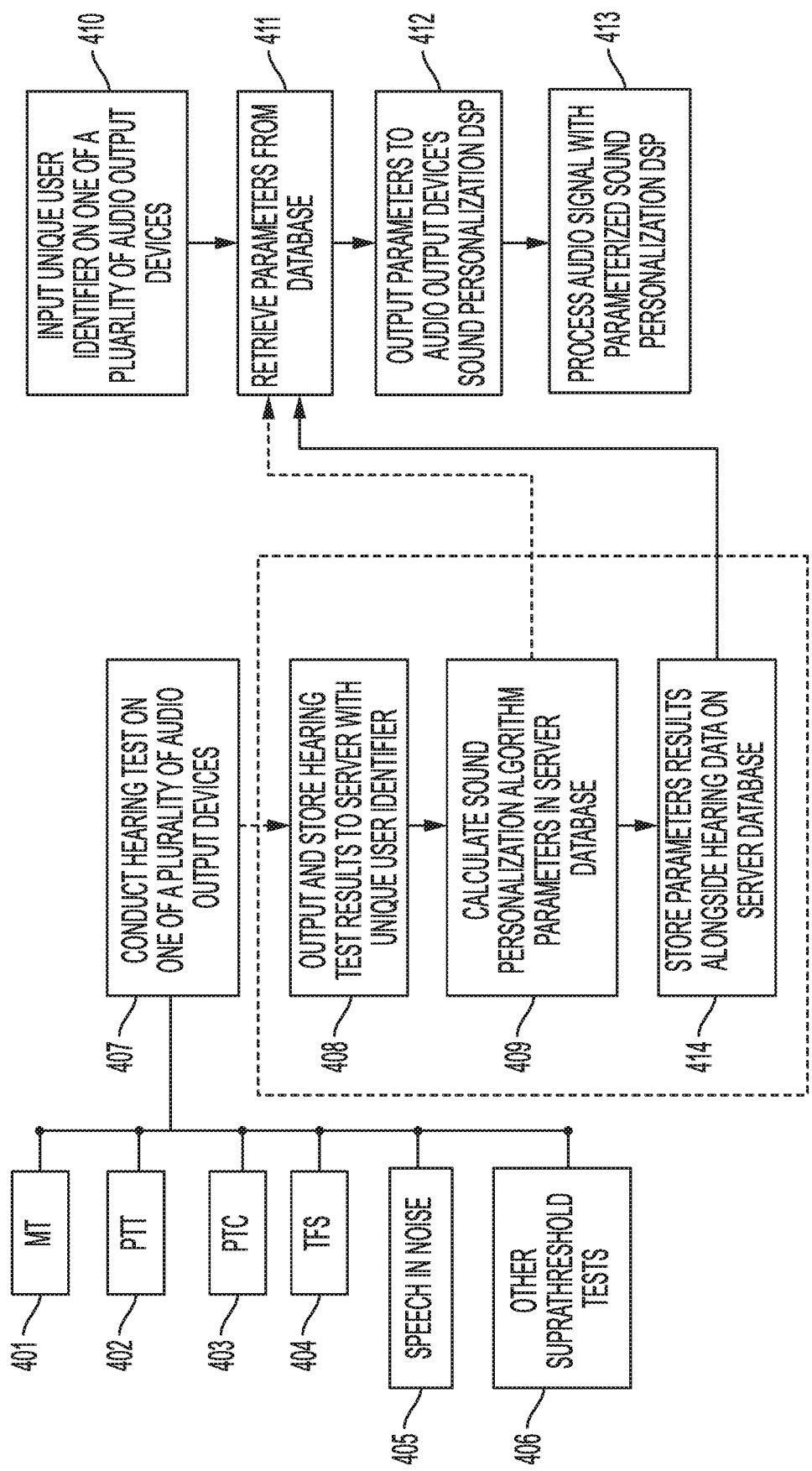

SYSTEMS AND METHODS FOR PROVIDING PERSONALIZED AUDIO REPLAY ON A PLURALITY OF CONSUMER DEVICES

FIELD OF INVENTION

This invention relates generally to the field of digital signal processing (DSP), audio engineering and audiology—more specifically systems and methods for providing server-mediated sound personalization on a plurality of consumer devices based on user hearing test results.

BACKGROUND

Traditional DSP sound personalization methods often rely on administration of an audiogram to parameterize a frequency gain compensation function. Typically, a pure tone threshold (PTT) hearing test is employed to identify frequencies in which a user exhibits raised hearing thresholds and the frequency output is modulated accordingly. These gain parameters are stored locally on the user's device for subsequent audio processing.

However, this approach to augmenting the sound experience for the user is imprecise and inefficient. As hearing test results are stored locally on a single device, the resulting parameter calculations are inaccessible to a central server, as well as other devices. To this extent, separate hearing tests must be conducted on every device—potentially leading to locally incorrect results and inconsistent parameter values stored on different audio output devices. The ability to take hearing tests on multiple devices linked to a core account: 1) encourages users to take tests on whatever device pairing is most convenient at the time, 2) improves accuracy through the consolidation of multiple test results, and 3) enables the tracking of a user's hearing state over time. Additionally, in the instance of aberrant hearing test results, the user can be informed if he or she is using an improperly calibrated device and/or if the hearing test was conducted improperly.

The use of frequency compensation is further inadequate to the extent that solely applying a gain function to the audio signal does not sufficiently restore audibility. The gain may enable the user to recapture previously unheard frequencies, but the user may subsequently experience loudness discomfort. Listeners with sensorineural hearing loss typically have similar, or even reduced, discomfort thresholds when compared to normal hearing listeners, despite their hearing thresholds being raised. To this extent, their dynamic aperture is narrower and simply adding gain would be detrimental to their hearing health in the long run.

Although hearing loss typically begins at higher frequencies, listeners who are aware that they have hearing loss do not typically complain about the absence of high frequency sounds. Instead, they report difficulties listening in a noisy environment and in hearing out the details in a complex mixture of sounds, such as in an audio stream of a radio interview conducted in a busy street. In essence, off frequency sounds more readily mask information with energy in other frequencies for hearing-impaired (HI) individuals—music that was once clear and rich in detail becomes muddled. This is because music itself is highly self-masking, i.e. numerous sound sources have energy that overlaps in the frequency space, which can reduce outright detectability, or impede the users' ability to extract information from some of the sources.

As hearing deteriorates, the signal-conditioning capabilities of the ear begin to break down, and thus HI listeners need to expend more mental effort to make sense of sounds of interest in complex acoustic scenes (or miss the information entirely). A raised threshold in an audiogram is not merely a reduction in aural sensitivity, but a result of the malfunction of some deeper processes within the auditory system that have implications beyond the detection of faint sounds. To this extent, the addition of simple frequency gain provides an inadequate solution Accordingly, it is an aspect of the present disclosure to provide systems and methods for providing personalized audio replay on a plurality of consumer devices through a server-empowered sound personalization account. By providing more accurate and portable parameter sets, a user may be able to enjoy sound personalization, and consequently, a healthier listening experience, across a universe of devices with one simple hearing test.

SUMMARY OF THE INVENTION

According to an aspect of the present disclosure, provided are systems and methods for providing personalized audio replay on a plurality of consumer devices. In some embodiments, the system and method include steps comprising: conducting a user hearing test on one of a plurality of audio output devices, outputting the hearing data from the user's hearing test to a server; storing the hearing data on the server's database with a user unique identifier; calculating a set of parameters from the user's hearing data for a sound personalization algorithm and storing the parameters alongside the unique user identifier on the database; outputting the set of parameters to the sound personalization algorithm on one of a plurality of audio output devices, wherein the parameters are outputted when the user inputs their unique identifier on one of the audio output devices; and processing an audio signal on one of the audio output devices using the sound personalization algorithm.

In another embodiment, the system and method include steps comprising: conducting a user hearing test on one of a plurality of audio output devices; calculating a set of parameters from the user's hearing data for a sound personalization algorithm on the audio output device; outputting the hearing data and calculated parameters to a server; storing the hearing data and calculated parameters on the server's database with a unique identifier; outputting the set of parameters to the sound personalization algorithm on one of a plurality of audio output devices, wherein the parameters are outputted when the user inputs their unique identifier to an application running on one of the audio output devices; and processing an audio signal on one of the audio output devices using the sound personalization algorithm.

In another embodiment, the system and method include steps comprising: conducting a user hearing test on one of a plurality of audio output devices; outputting the hearing data of the user's hearing test to a server; storing the hearing data on the server's database with a unique identifier; outputting the hearing data to one of a plurality of audio output devices, wherein the hearing data is outputted when the user inputs their unique identifier to an application running on one of the audio output devices; calculating a set of parameters from the user's hearing data for a sound personalization algorithm on the audio output device; and outputting the parameters to the sound personalization algorithm on the audio output device.

In some embodiments, the hearing test is one or more of a threshold test, a suprathreshold test, a psychophysical tuning curve test, a masked threshold test, a temporal fine structure test, a speech in noise test and a temporal masking curve test.

In some embodiments, the parameters are recalculated when the user conducts an additional hearing test on anyone of a plurality of audio output devices. The additional hearing test may reflect information from another critical band. The additional hearing test may be a different type of hearing test from previously conducted hearing tests or it may be a more recent version of a previously conducted hearing test. Additionally, the additional hearing test may replace the hearing data from a previously conducted hearing test with aberrant results.

In some embodiments, the set of parameters is calculated on demand on the server when the user inputs their unique identifier on one of the audio output devices.

In some embodiments, the hearing test measures masking threshold curves within a range of frequencies from 250 Hz to 12 kHz.

In some embodiments, the sound personalization algorithm operates on subband signals of the audio signal, i.e. the algorithm works frequency selectively. In a further embodiment, the parameters of the sound personalization algorithm comprise at least one of a gain value provided in each subband and a limiter value provided in each subband. In an optional embodiment, the sound personalization algorithm may be a multiband dynamic processing algorithm. The parameters of the multiband dynamics processor may optionally comprise at least one of a threshold value of a dynamic range compressor provided in each subband, a ratio value of a dynamic range compressor provided in each subband, and a gain value provided in each subband. In an alternate embodiment, the parameters of the multiband dynamics processor may optionally be determined from a hearing aid gain table, which specify the amount of gain for a given input level at each frequency. Typically these tables comprise columns for frequencies and rows for varying intensities of sound inputs (which also may be mapped to threshold, ratio and gain settings overall).

In some embodiments, the parameters are calculated indirectly. For instance, parameters may be calculated using a best fit of the user hearing data with previously inputted entries within the server's database, wherein the parameters associated with the best fitting, previously inputted hearing data are copied and inputted into the user's server database entry. Best fit may be determined, for instance, by measuring average Euclidean distance between the user's hearing data and hearing data in the database. Alternatively, root mean square distance or a similar best fit measurement may be used.

In some embodiments, the parameters may be calculated using the nearest fit of the user hearing data with at least two hearing data entries within the server's database, wherein the parameters associated with the nearest fitting, previously inputted hearing data are interpolated and inputted into the user's server database entry. For instance, parameters may be interpolated linearly between two parameter values. Alternately, parameters may be interpolated non-linearly, such as through a squared function. Alternately, the parameters may be calculated from a fitted mathematical function, such as a polynomial function, derived from plotting existing hearing and parameter set data entries within the server database.

In some embodiments, the parameters may be calculated by converting the user's hearing test results into a 'hearing age' value. Based upon predictable declines in hearing function, the user's hearing test results may be matched to the nearest representative hearing age. From this, hearing age parameter sets are then copied into the user's hearing profile.

In some embodiments, the parameters may be calculated directly. For instance, the parameters may be calculated by fitting a user masking contour curve to a target masking contour curve. Alternately, the parameters may be calculated through the optimization of perceptually relevant information (PRI). Alternately, the parameters may be calculated using commonly known prescriptive techniques in the art.

In some embodiments, the consumer electronic device is one of a mobile phone, a tablet, a television, a desktop computer, a laptop, a hearable, a smart speaker, a headphone and a speaker system.

Unless otherwise defined, all technical terms used herein have the same meaning as commonly understood by one of ordinary skill in the art to which this technology belongs.

The term "sound personalization algorithm", as used herein, is defined as any digital signal processing (DSP) algorithm that processes an audio signal to enhance the clarity of the signal to a listener. The DSP algorithm may be, for example: an equalizer, an audio processing function that works on the subband level of an audio signal, a multiband compressive system, or a non-linear audio processing algorithm.

The term "audio output device", as used herein, is defined as any device that outputs audio, including, but not limited to: mobile phones, computers, televisions, hearing aids, headphones, smart speakers, hearables, and/or speaker systems.

The term "headphone", as used herein, is any earpiece bearing a transducer that outputs soundwaves into the ear. The earphone may be a wireless hearable, a corded or wireless headphone, a hearable device, or any pair of earbuds.

The term "hearing test", as used herein, is any test that evaluates a user's hearing health, more specifically a hearing test administered using any transducer that outputs a sound wave. The test may be a threshold test or a suprathreshold test, including, but not limited to, a psychophysical tuning curve (PTC) test, a masked threshold (MT) test, a temporal fine structure test (TFS), temporal masking curve test and a speech in noise test.

The term "server", as used herein, generally refers to a computer program or device that provides functionalities for other programs or devices.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understand that these drawings depict only exemplary embodiments of the disclosure and are not therefore to be considered to be limiting of its scope, the principles herein are described and explained with additional specificity and detail through the use of the accompanying drawings in which:

FIG. 4 illustrates a method for server-side management of personalized audio replay on a plurality of consumer devices according to one or more aspects of the present disclosure;

DETAILED DESCRIPTION

Figure 1:
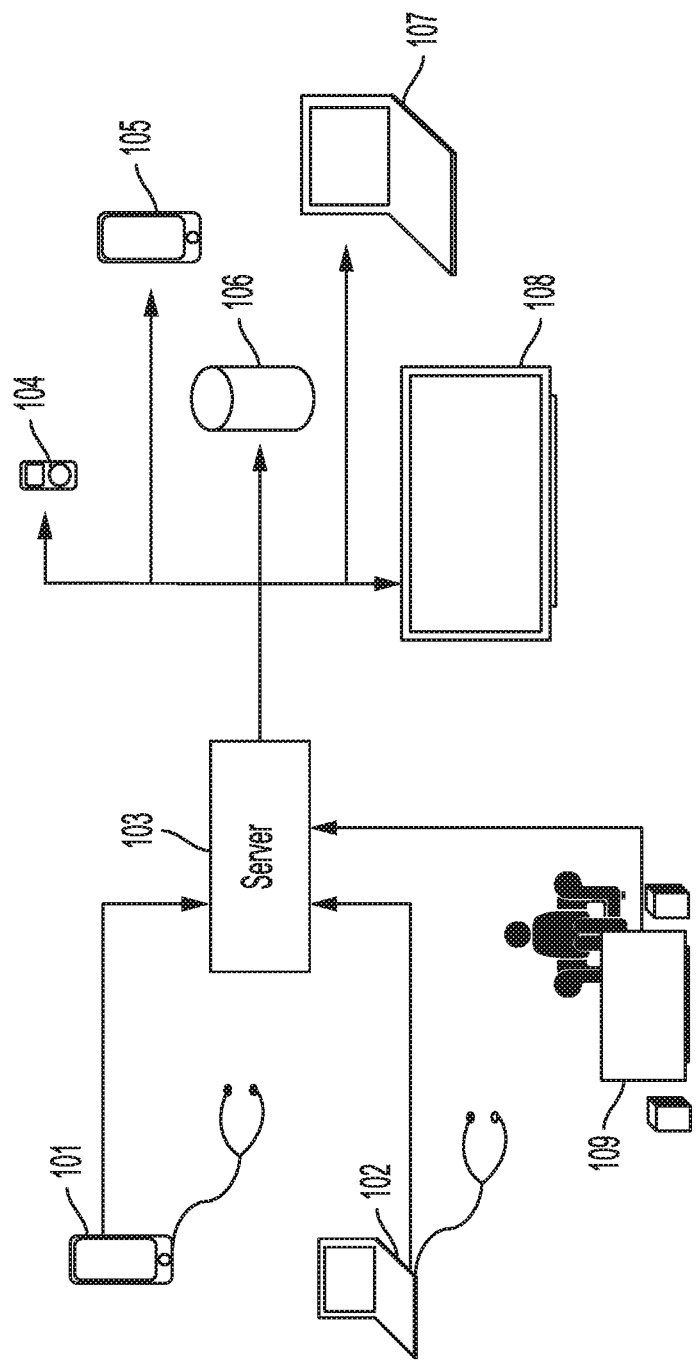
FIG. 1 illustrates a flow chart of a server receiving hearing test data input from a plurality of devices and outputting sound personalization DSP parameters to a plurality of audio output devices.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting the scope of the embodiments described herein. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Various example embodiments of the disclosure are discussed in detail below. While specific implementations are discussed, it should be understood that this is done for illustration purposes only. A person skilled in the relevant art will recognize that other components and configurations may be used without departing from the spirit and scope of the present disclosure.

The systems and methods according to aspects of the present disclosure address the problems of accurately and effectively personalizing the audio output of a plurality of audio output devices, and particularly the problem of doing so in a consistent manner. By enabling server-mediated sound personalization based on user hearing test results, aspects of the present disclosure provide for seamless sound personalization between various audio output devices. To this extent, increased user adoption of sound personalization and/or augmentation will not only enable a richer and crisper listening experience for the user, but also lead to healthier user behavior while listening to audio.

As illustrated in FIG. 1, a user may take a hearing test, for instance, on a mobile phone 101, laptop computer 102 or in front of a television 109, the results of which may then be outputted to a server 103. The resulting DSP parameters may then be calculated and stored on the server 103. This DSP parameter calculation may be done on the initial device (e.g., 101, 102, 103) on which the hearing test is conducted, on the server 103, or some combination of the above. The resulting DSP parameters may then be outputted to a plurality of end user devices, which include, but are not limited to, a media player 104, mobile phone 105, smart speaker 106, laptop computer 107, and a television set 108, etc. The calculated DSP parameters are subsequently used to provide seamless and consistent sound personalization across each of the various end user devices 104-108. In some embodiments, a user's hearing test data is outputted to one or more of the end user devices 104-108, such that the DSP parameter calculation may be performed on the end user device. In some embodiments, one or more of the end user devices 104-108 can be employed to perform the user hearing test, i.e. the initial device 101-103 and the end user device 104-108 can be provided as a single device.

Figure 2A:
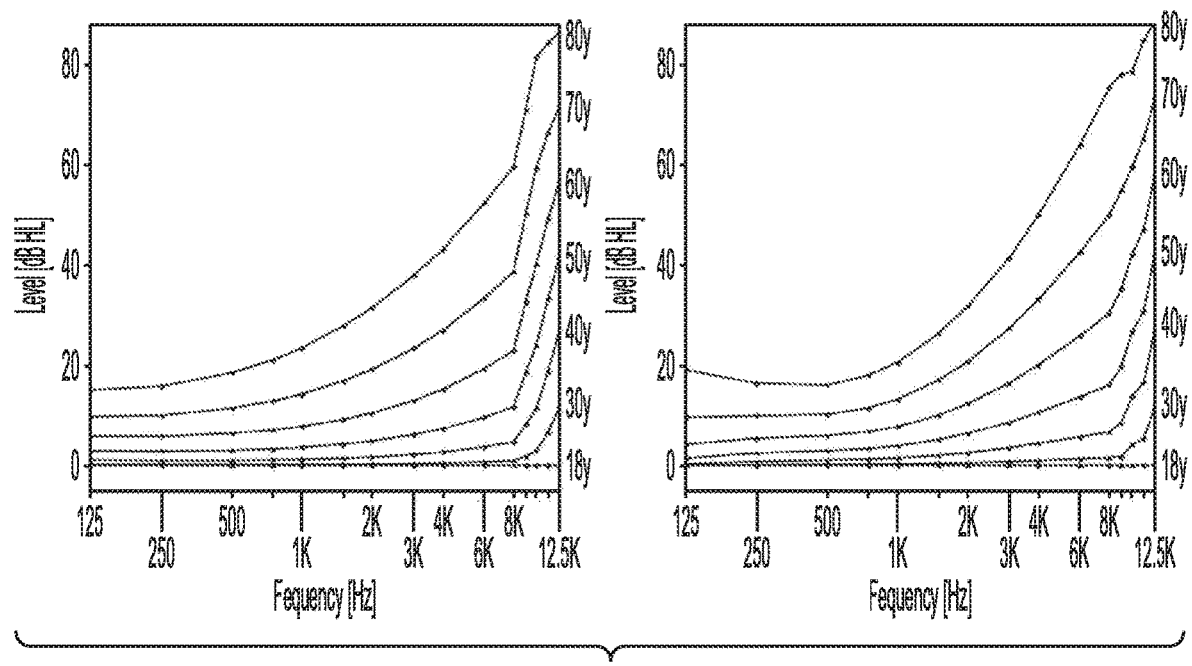
FIGS. 2A and 2B illustrate example graphs showing the deterioration of human audiograms and masking thresholds with age, respectively.
Figure 2B:
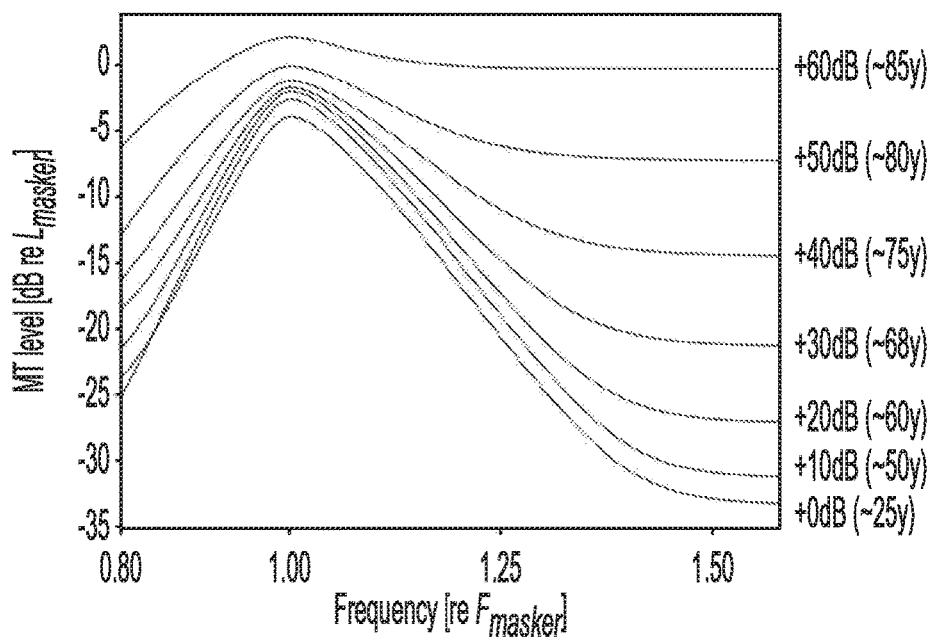

FIGS. 2A-B underscore the importance of sound personalization, illustrating the deterioration of a listener's hearing ability over time. Starting at the age of 20 years old, humans begin to lose their ability to hear higher frequencies—FIG. 2A (albeit above the spectrum of human speech). This loss steadily becomes worse with age, as noticeable declines within the speech frequency spectrum are apparent around the age of 50 or 60. However, these pure tone audiometry findings mask a more complex problem as the human ability to understand speech may decline much earlier. Although hearing loss typically begins at higher frequencies, listeners who are aware that they have hearing loss do not typically complain about the absence of high frequency sounds. Instead, they report difficulties listening in a noisy environment and in hearing out the details in a complex mixture of sounds, such as in a telephone call. In essence, off-frequency sounds more readily mask a frequency of interest for hearing impaired individuals—conversation that was once clear and rich in detail becomes muddled. As hearing deteriorates, the signal-conditioning capabilities of the ear begin to break down, and thus hearing impaired listeners need to expend more mental effort to make sense of sounds of interest in complex acoustic scenes (or miss the information entirely). A raised threshold in an audiogram is not merely a reduction in aural sensitivity, but a result of the malfunction of some deeper processes within the auditory system that have implications beyond the detection of faint sounds.

To this extent, FIG. 2B illustrates key, discernable age trends in suprathreshold hearing tests. The psychophysical tuning curve (PTC) test is a suprathreshold test that measures an individual's ability to discern a probe tone (or pulsed signal tone) against a sweeping masker noise of variable frequency and amplitude. For example, the psychophysical tuning curve test may be measured for signal tones between frequencies of 500 Hz and 4 kHz, and at a probe level of between 20 dB SL and 40 dB SL, in the presence of a masking signal for the signal tone that sweeps from 50% of the signal tone frequency to 150% of the signal tone frequency. Additionally, while the sound level of the probe tone may be between 20 dB SL and 40 dB SL (although various other ranges, such as 5 dB SL-40 dB SL, are also possible), it is noted that the sound level of the sweeping masking signal can exceed, and even significantly exceed, the sound level range associated with the probe tone. Through the collection of large datasets, key age trends as seen on the rightmost vertical axis in FIG. 2B can be ascertained, allowing for the accurate parameterization of personalization DSP algorithms. In a multiband compressive system, for example, the threshold and ratio values of each subband signal dynamic range compressor (DRC) can be modified to reduce problematic areas of frequency masking, while post-compression subband signal gain can be further applied in the relevant areas. In the context of FIGS. 2A-B, masked threshold curves represent a similar paradigm for measuring masked threshold. A narrow band of noise, in this instance around 4 kHz, is fixed while a probe tone sweeps from 50% of the noise band center frequency to 150% of the noise band center frequency. Again, key age trends can be ascertained from the collection of large MT datasets.

Figure 3B:
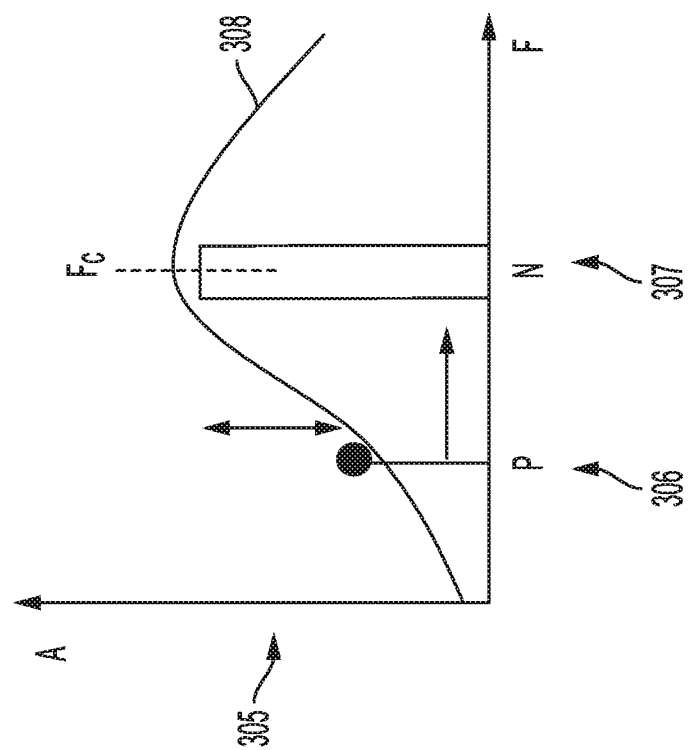
FIGS. 3A and 3B illustrate example graphs showing one example of the PTC and MT test paradigms.
Figure 3A:
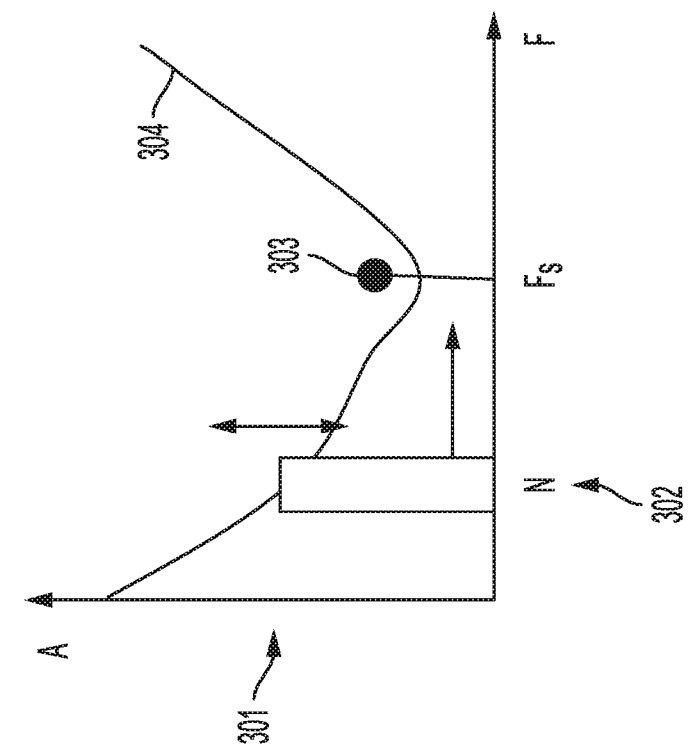

FIGS. 3A-B illustrate graphs showing an example method in which a PTC test 301 or MT test 305 may be conducted. A psychophysical tuning curve (PTC), consisting of a frequency selectivity contour 304, extracted via behavioral testing, provides useful data to determine an individual's masking contours. In one embodiment of the test, a masking band of noise 302 is gradually swept across frequency, from below the probe frequency 303 to above the probe frequency 303. The user then responds when they can hear the probe and stops responding when they no longer hear the probe. This gives a jagged trace that can then be interpolated to estimate the underlying characteristics of the auditory filter through a masking contour curve plot. Other methodologies known in the prior art may be employed to attain user masking contour curves. For instance, an inverse paradigm may be used in which a probe tone 306 is swept across frequency while a masking band of noise 307 is fixed at a center frequency (known as a "masked threshold test" or "MT test").

FIG. 4 illustrates an exemplary embodiment of the present disclosure in which personalized audio replay is carried out on a plurality of audio output devices. First, a hearing test is conducted 407 on one of a plurality of audio output devices. The hearing test may be provided by any one of a plurality of hearing test options, including but not limited to: a masked threshold test (MT test) 401, a pure tone threshold test (PTT test) 402, a psychophysical tuning curve test (PTC test) 403, a temporal fine structure test (TFS test) 404, a speech in noise test 405, or other suprathreshold test(s) 406.

Next, hearing test results are outputted 408 to a server along with one or more of a timestamp and a unique user identifier. DSP parameters for a sound personalization algorithm are then calculated and stored 409 in the server database. The calculated DSP parameters for a given sound personalization algorithm may include, but are not limited to: ratio, threshold and gain values within a multiband dynamic processor, gain and limiter values for equalization DSPs, and/or parameter values common to other sound personalization DSPs (see, e.g., commonly owned U.S. Pat. No. 10,199,047 and U.S. patent application Ser. No. 16/244,727, the contents of which are incorporated by reference in their entirety).

One or more of the DSP parameter calculations may be performed directly or indirectly, as is explained below. When a user inputs 410 their unique identifier on one of a plurality of audio output devices, the user's DSP parameters are retrieved 411 from the server database and outputted 412 to the audio output device's sound personalization DSP. The user's unique identifier may be entered into a standalone application on the user's device—or alternatively or additionally, may be entered into an existing application with a plugin sign-in functionality that mediates server connectivity. After the user's unique identifier has been received and the corresponding DSP parameter's retrieved from the server database, audio signals are then locally processed 413 at the given audio output device using the parameterized sound personalization DSP.

Figure 5:
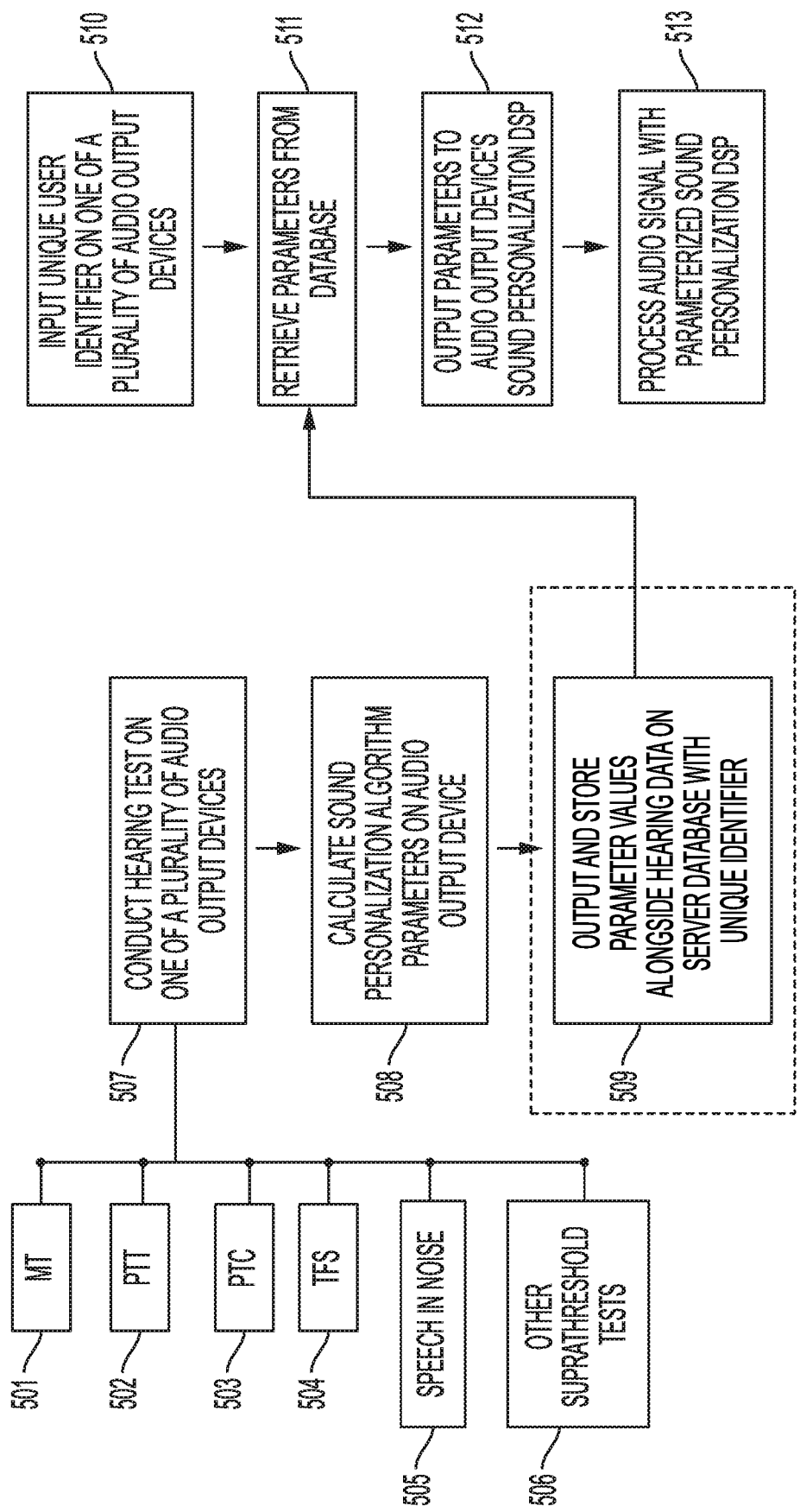
FIG. 5 illustrates a method for server-side management of personalized audio replay on a plurality of consumer devices according to one or more aspects of the present disclosure.

FIG. 5 illustrates an alternative embodiment to the method illustrated in FIG. 4. As depicted in FIG. 5, a hearing test (e.g. selected from the group of hearing tests 501-506, which in some embodiments can be the same as the group of hearing tests 401-406) is first conducted 507 on one of a plurality of audio output devices. After conducting the hearing test, the audio output device then calculates 508 the DSP parameters itself and outputs 509 these locally calculated DSP parameter values and the user's hearing data to the server database. This output is then stored 509 at the server database alongside the user's unique identifier.

In contrast to the embodiment of FIG. 4, where the server received the user's hearing test data and then performed a server-side calculation of the DSP parameters, the embodiment of FIG. 5 performs local calculation of the DSP parameters (i.e. on the same audio output device where the hearing test was performed/measured). However, because the audio output device transmits both the locally calculated DSP parameters and the underlying hearing test data to the server, it is still possible for a server-side calculation of the DSP parameters to be performed. For example, such a server-side calculation might be used to verify or otherwise augment the local calculation, or as a backup measure.

Subsequently, in a similar fashion to the embodiment of FIG. 4, when a user inputs 510 their unique identifier in an application on one of a plurality of audio output devices, their DSP parameters are retrieved 511 from the server database and outputted 512 to the audio output device's sound personalization DSP. Audio signals are then processed 513 accordingly.

Figure 6:
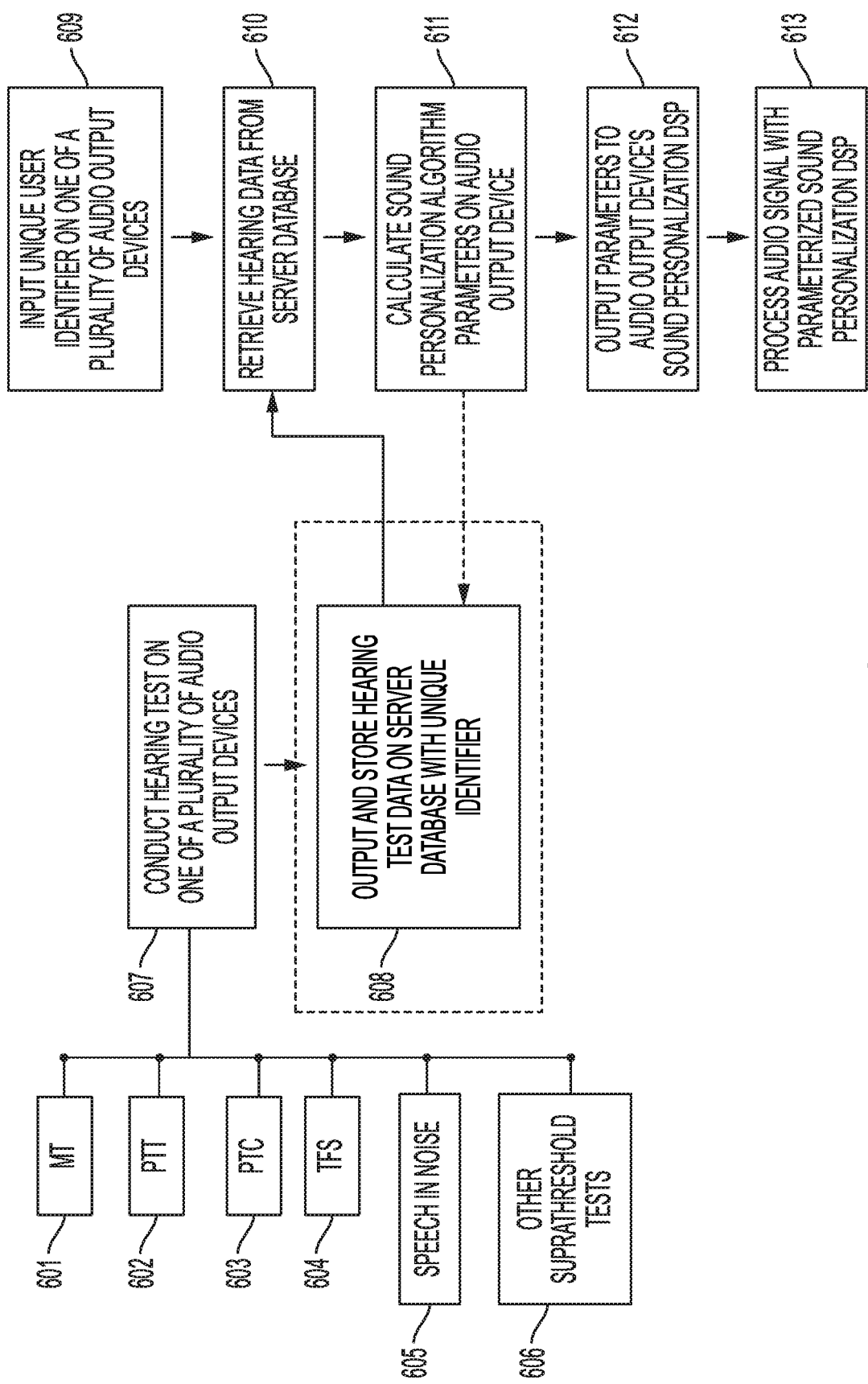
FIG. 6 illustrates a method for server-side management of personalized audio replay on a plurality of consumer devices according to one or more aspects of the present disclosure.

FIG. 6 illustrates a further alternative embodiment to the methods illustrated in FIGS. 4 and 5. Here, a hearing test is conducted on one of a plurality of audio output devices 607 and subsequently, the hearing test data is stored 608 on a server database with a unique user identifier. In the embodiment of FIG. 6, DSP parameters for the hearing test data are not necessarily calculated in response to the hearing test data being received at the server or server database. Notably, DSP parameters can instead be calculated 611 in an on-demand or just-in-time fashion, either on the end user device, the server, or some combination of the two, wherein the calculation 611 is based on hearing data that is retrieved 610 from the server database when a user inputs 609 their unique identifier on the end user device. The calculated DSP parameters may optionally be outputted to the server for storage alongside the user's hearing data.

Importantly, the previously discussed methods illustrated in FIGS. 4-6 commonly feature a central server which mediates the exchange of data necessary for sound personalization across a plurality of audio output devices, independent of when and where the calculation of the DSP parameter values is performed.

Figure 7:
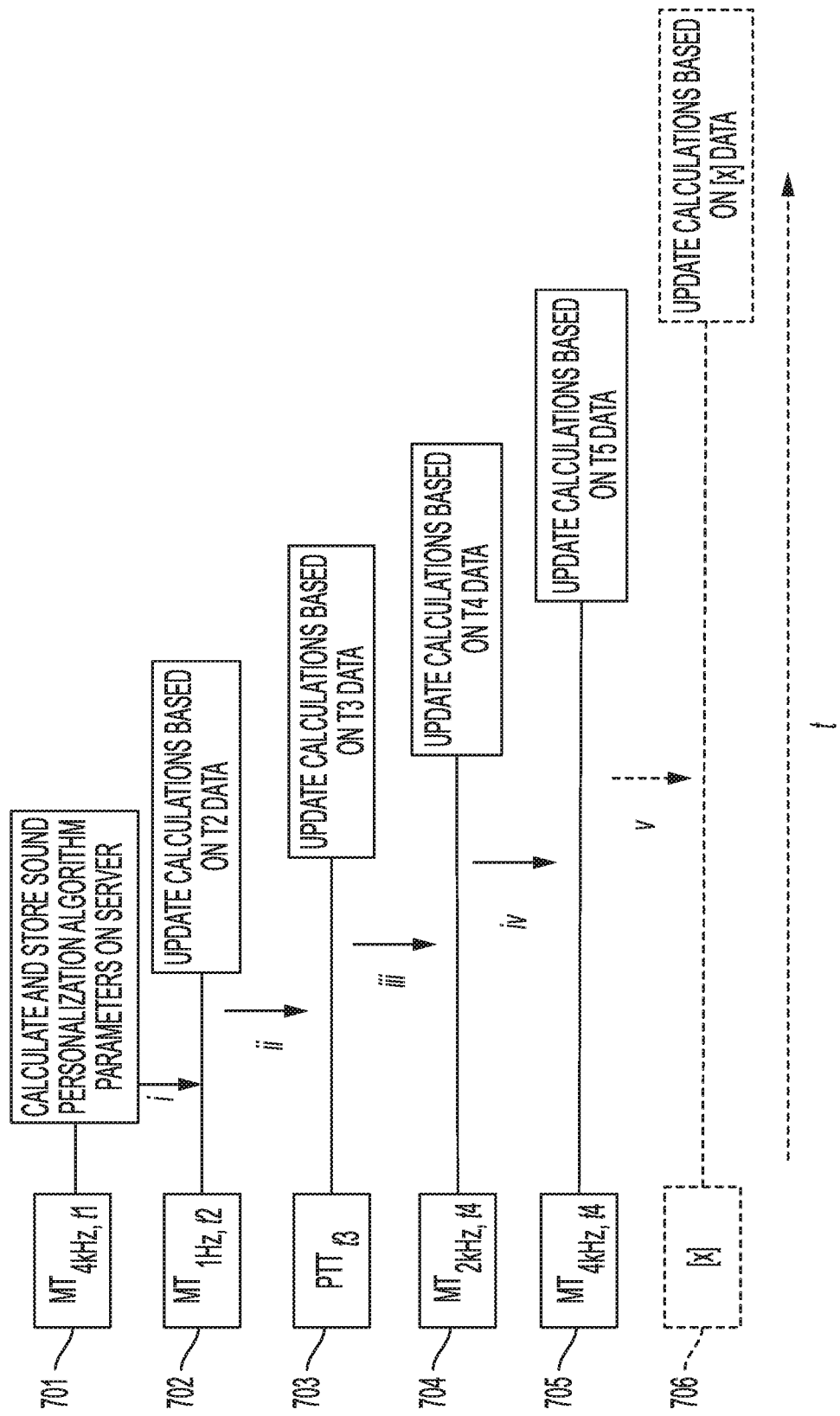
FIG. 7 illustrates a method for server-side management of personalized audio replay in which a user's parameter settings are updated based on taking multiple hearing tests over a period of time.

FIG. 7 illustrates a further example embodiment demonstrating the manner in which a user's calculated DSP parameters may change over time, e.g., in this case when a user takes multiple hearing tests. As depicted in FIG. 7, at t1 a user takes an MT test with a 4 kHz noise probe 701 and DSP parameters are then calculated and stored based on the hearing data from the MT test, for example, according to any of the methods illustrated in FIGS. 4-6. Next, at t2, the user takes an MT test with a 1 kHz noise probe 702, representing hearing data within another auditory filter region of the individual. Taken together with data collected at t1, the combination of both data sets may provide a more comprehensive picture of the user's hearing health, thus enabling a more accurate calculation of DSP parameters. To this extent, DSP parameters are updated in view of the t1 and t2 data. The user may then take further tests, such as a pure tone threshold test 703 or an MT test with a 2 kHz noise probe 704 to further refine their hearing profile. Additionally, the user may retake a test 705 at a later time point t5, which may reveal that an earlier test result was aberrant and/or that the user's hearing ability has degraded since the previous test—both scenarios resulting in a parameter update based on the new results. Altogether, the method illustrated in FIG. 7 provides for an evolving and accurate hearing profile that informs updated calculations for sound personalization algorithms.

Figure 8:
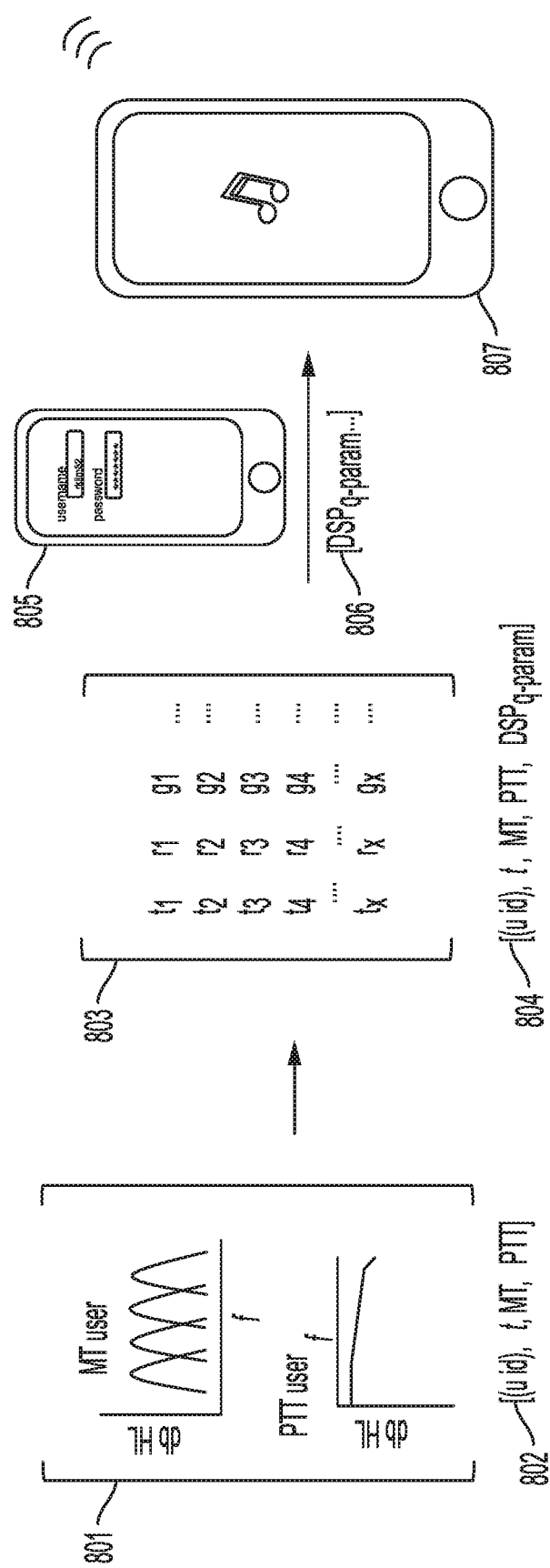
FIG. 8 illustrates a method in which a threshold and suprathreshold test are used to calculate sound personalization parameters.

FIG. 8 further illustrates an example embodiment for personalizing audio replay according to aspects of the present disclosure. Hearing test data 801 is obtained from a user and is utilized to calculate sound personalization DSP parameters 803, in this instance, for a multiband dynamics processor with at least parameter values ratio (r), threshold (t) and gain (g) for each subband 1 through x. Here, the hearing test data 801 is provided as MT and PTT data, although other types of hearing test data can be utilized without departing from the scope of the present disclosure. Within the server, hearing data may be stored as exemplary entry [(u_id), t, MT, PTT] 802, wherein u_id is a unique user ID, t is a timestamp, MT is hearing data related to an MT test, and PTT is hearing data related to a PTT test. Additionally, when DSP parameter sets are calculated for a given sound personalization algorithm, they may then be added to the entry as [$DSP_{q\text{-}param}$] 804. When a user subsequently inputs their u_id to log in to a given application on their audio output device 805, [$DSP_{q\text{-}param}$] 806 corresponding to the u_id are then outputted to the audio output device 807. In FIG. 8, parameter set values 803 encompass at least ratio and threshold values for a dynamic range compressor as well as gain values per subband signal from 1 to x in a multiband dynamics processor sound personalization algorithm.

In some embodiments, DSP parameter sets may be calculated directly from a user's hearing data or calculated indirectly based on preexisting entries or anchor points in the server database. An anchor point comprises a typical hearing profile constructed based at least in part on demographic information, such as age and sex, in which DSP parameter sets are calculated and stored on the server to serve as reference markers. Indirect calculation of DSP parameter sets bypasses direct parameter sets calculation by finding the closest matching hearing profile(s) and importing (or interpolating) those values for the user.

Figure 9:
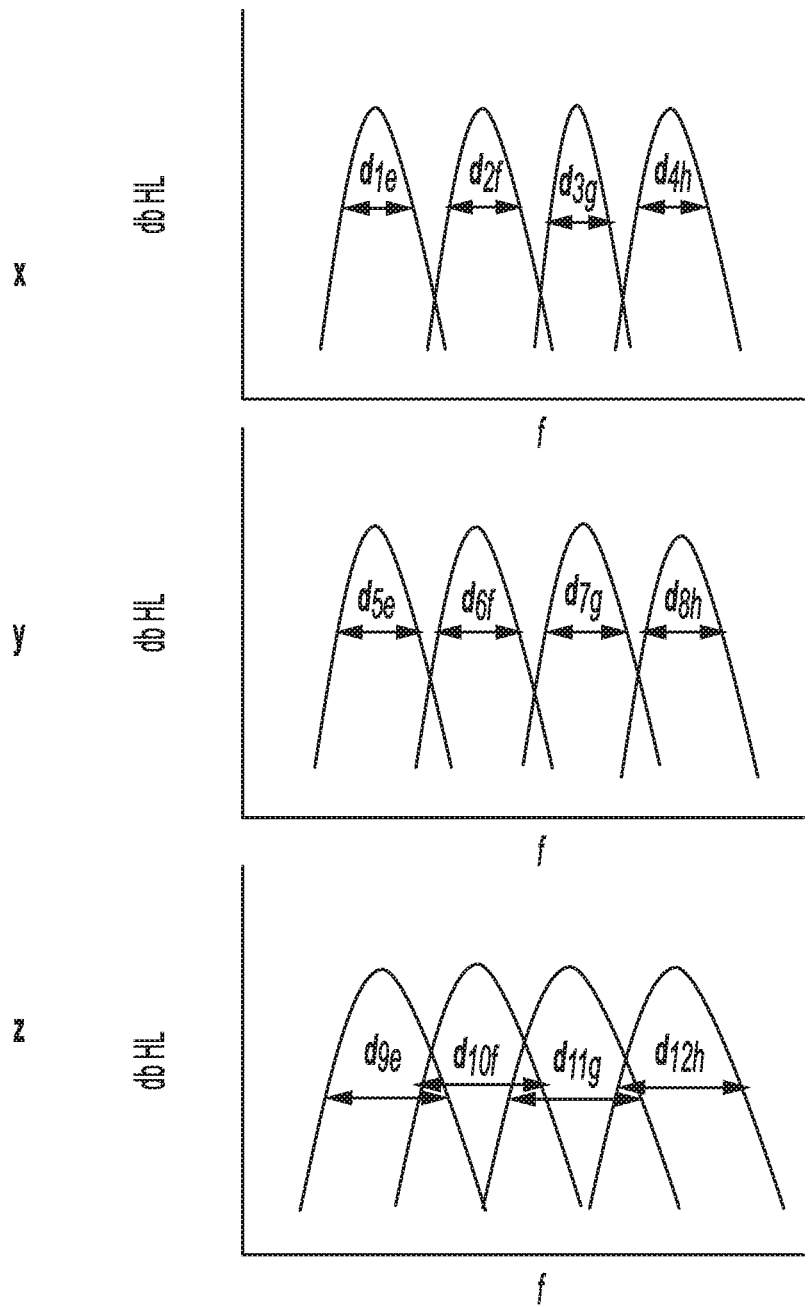
FIG. 9 conceptually illustrates masked threshold curve widths for three different users, which can be used for best fit and/or nearest fit calculations.

FIG. 9 illustrates three conceptual user masked threshold (MT) curves for users x, y, and z. The MT curves are centered at frequencies a-d, each with curve width d, which may be used to as a metric to measure the similarity between user hearing data. For instance, a root mean square difference calculation may be used to determine if user y's hearing data is more similar to user x's or user z's, e.g. by calculating:

$$\sqrt{(d5a-d1a)^2+(d6b-d2b)^2...}<\sqrt{(d5a-d9a)^2+(d6b-d10b)^2...}$$

Figure 10:
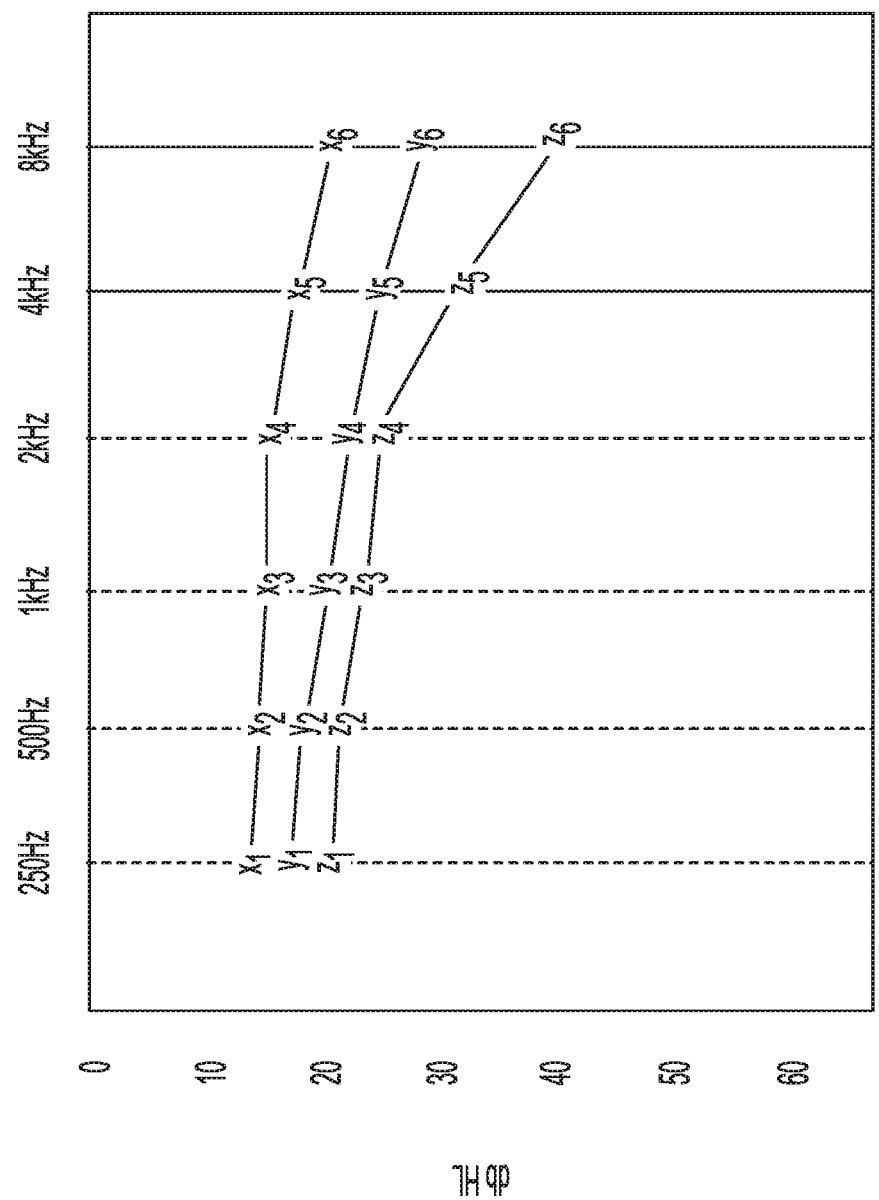
FIG. 10 conceptually illustrates audiogram plots for three different users x, y and z, data points which can be used for best fit and/or nearest fit calculations.

FIG. 10 illustrates three conceptual audiograms of users x, y and z, each with pure tone threshold values 1-5. Similar to above, a root mean square difference measurement may also be used to determine, for example, if user y's hearing data is more similar to user x's than user z's, e.g., by calculating:

$$(\sqrt{(y1-x1)^2+(y2-x2)^2...}<\sqrt{(y1-z1)^2+(y2-z2)^2...})$$

As would be appreciated by one of ordinary skill in the art, other methods may be used to quantify similarity amongst user hearing profile graphs, where the other methods can include, but are not limited to, methods such as a Euclidean distance measurements, e.g. $((y1-x1)+(y2-x2)\ldots>(y1-x1)+(y2-x2))\ldots$ or other statistical methods known in the art. For indirect DSP parameter set calculation, then, the closest matching hearing profile(s) between a user and other preexisting database entries or anchor points can then be used.

Figure 11:
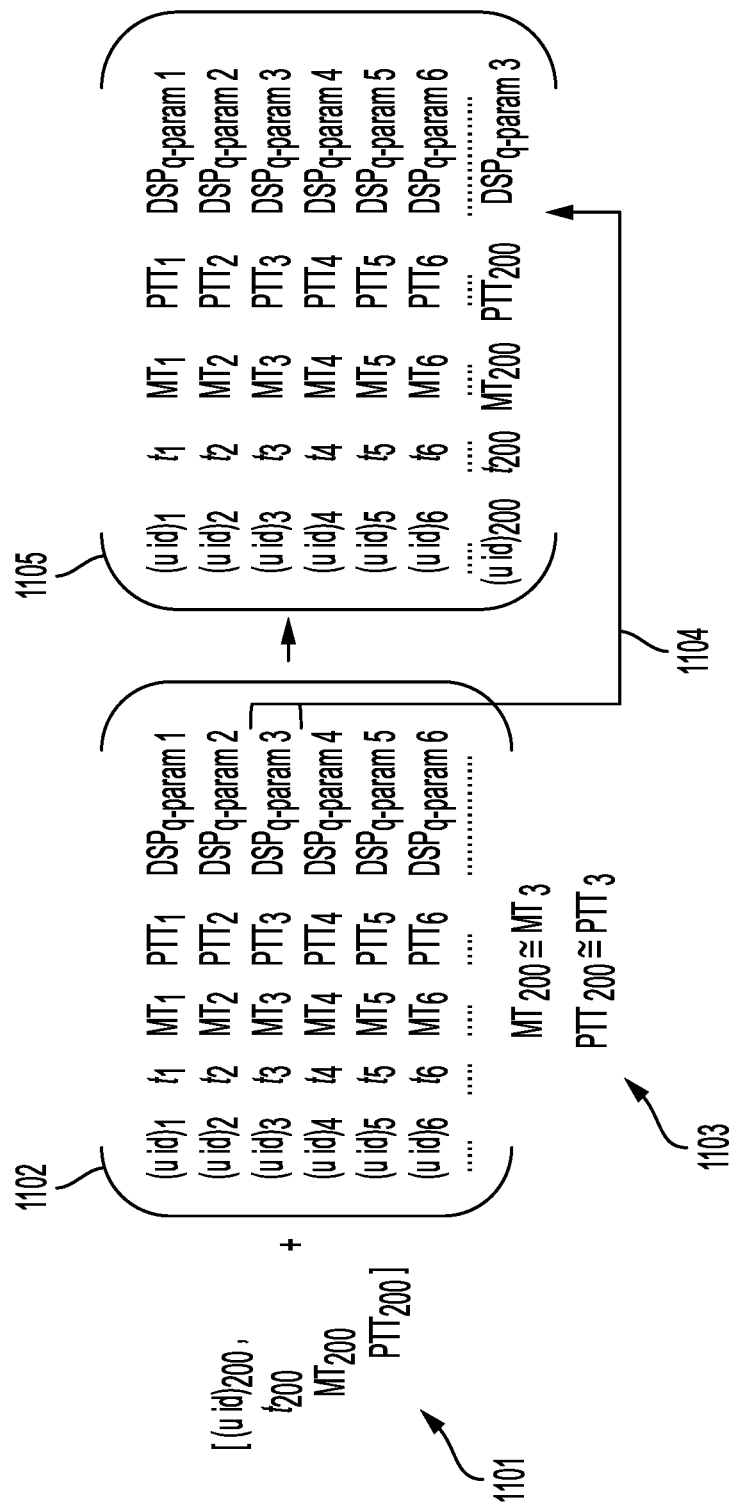
FIG. 11 illustrates a method for parameter calculation using a best-fit approach.

FIG. 11 illustrates an exemplary embodiment for calculating sound personalization parameter sets for a given algorithm based on preexisting entries and/or anchor points. Here, server database entries 1102 are surveyed to find the best fit(s) with user hearing data input 1101, represented as $MT_{200}$ and $PTT_{200}$ for $(u\_id)_{200}$. This may be performed by the statistical techniques illustrated in FIGS. 9 and 10. In the example of FIG. 11, $(u\_id)_{200}$ hearing data best matches $MT_3$ and $PTT_3$ data 603. To this extent, $(u\_id)_3$ associated parameter sets, $[DSP_{q\text{-}param\ 3}]$, are then used for the $(u\_id)_{200}$ parameter set entry, illustrated here as $[(u\_id)_{200}, t_{200}, MT_{200}, PTT_{200}, DSP_{q\text{-}param\ 3}]$.

Figure 12:
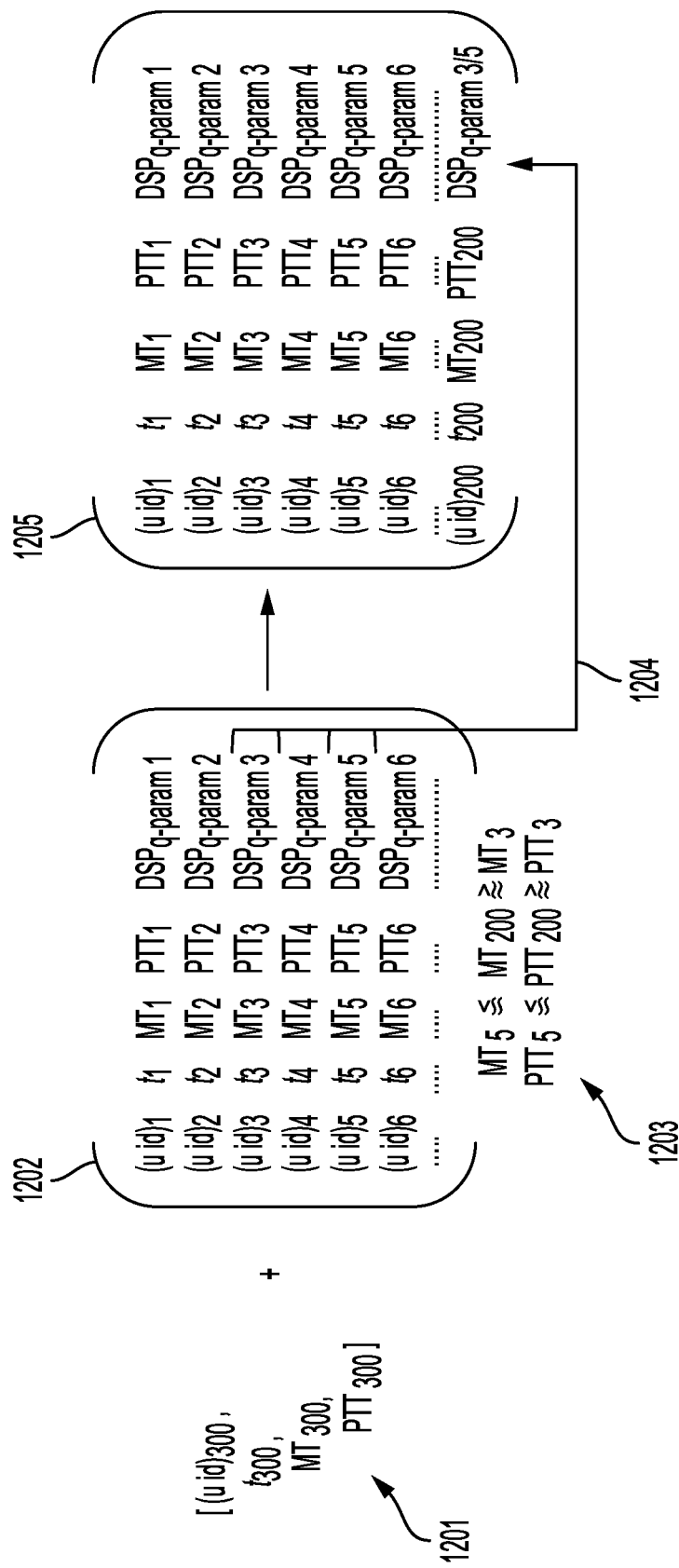
FIG. 12 illustrates a method for parameter calculation using an interpolation of nearest-fitting hearing data.

FIG. 12 illustrates an exemplary embodiment for calculating sound personalization parameter sets for a given algorithm based on preexisting entries or anchor points, according to aspects of the present disclosure. Here, server database entries 1202 are employed to interpolate 1204 between two nearest fits 1200 with user hearing data input 1201 $MT_{300}$ and $PT_{300}$ for $(u\_id)_{300}$. In this example, the $(u\_id)_{300}$ hearing data fits nearest between: $MT_5 \lesssim MT_{200} \gtrsim MT_3$ and $PTT_5 \lesssim PTT_{200} \gtrsim PTT_3$ 703. To this extent, $(u\_id)_3$ and $(u\_id)_5$ parameter sets are interpolated to generate a new set of parameters for the $(u\_id)_{300}$ parameter set entry, represented here as $[(u\_id)_{200}, t_{200}, MT_{200}, PTT_{200}, DSP_{q\text{-}param3/5}]$ 705. In a further embodiment, interpolation may be performed across multiple data entries to calculate sound personalization parameters, e.g/

DSP parameter sets may be interpolated linearly, e.g., a DRC ratio value of 0.7 for user 5 $(u\_id)_5$ and 0.8 for user 3 $(u\_id)_3$ would be interpolated as 0.75 for user 200 $(u\_id)_{200}$ in the example of FIG. 12, assuming user 200's hearing data was halfway in-between that of users 3 and 5. In some embodiments, DSP parameter sets may also be interpolated non-linearly, for instance using a squared function, e.g. a DRC ratio value of 0.6 for user 5 and 0.8 for user 3 would be non-linearly interpolated as 0.75 for user 200 in the example of FIG. 12.

Figure 13:
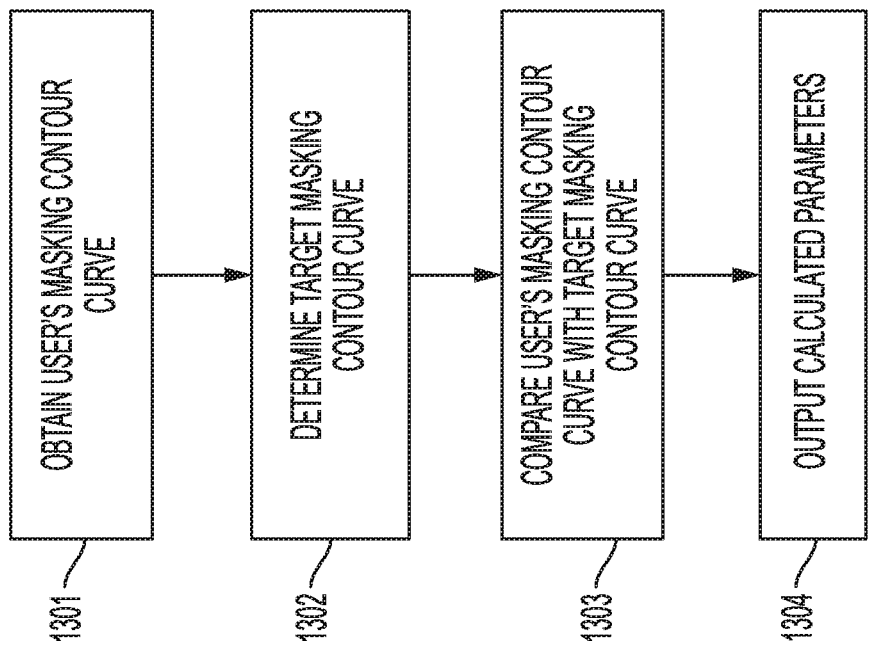
FIG. 13 illustrates a method of attaining ratio and threshold parameters from a user masking contour curve.
Figure 14:
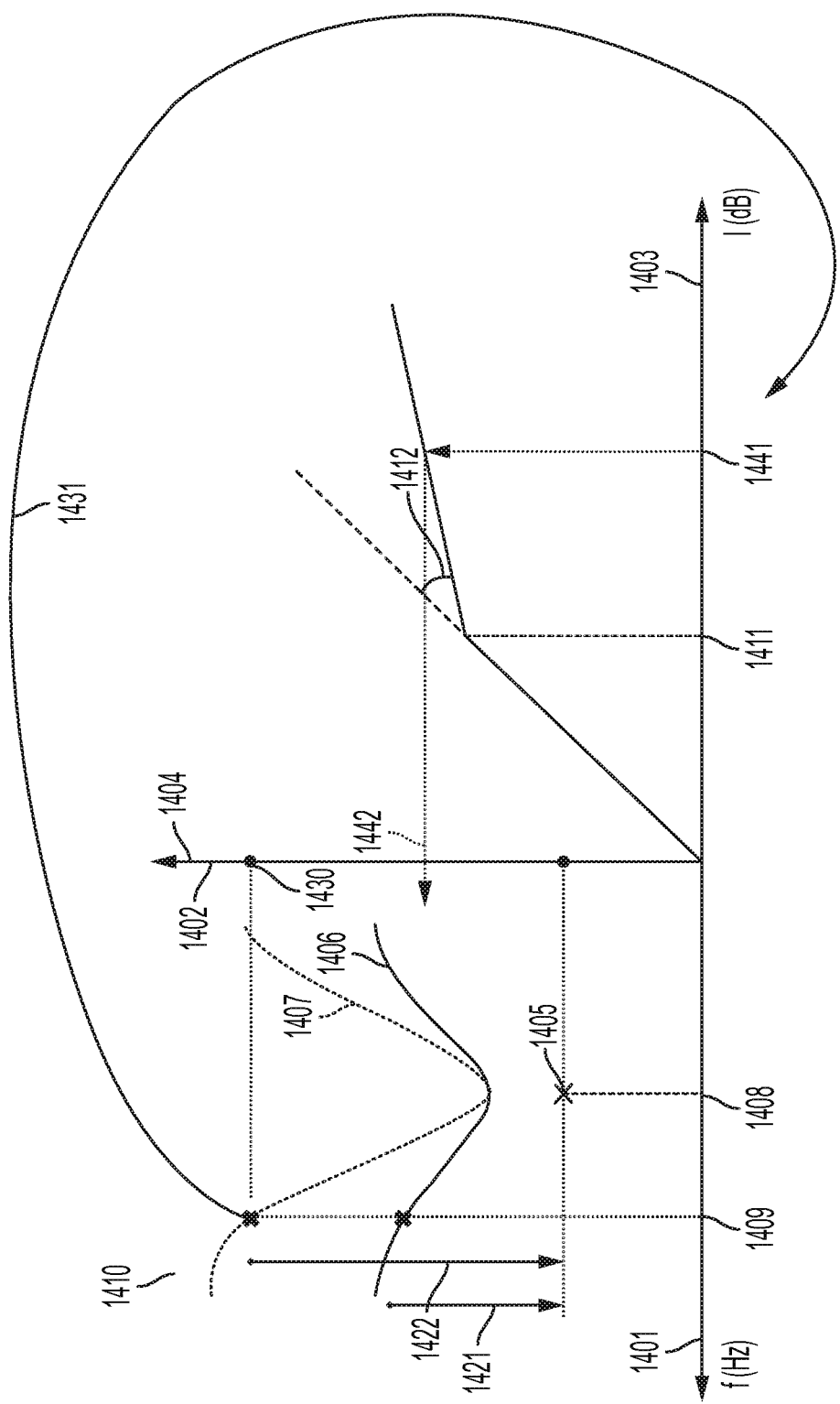
FIG. 14 illustrates a graph for attaining ratio and threshold parameters from a user PTC curve.
Figure 15:
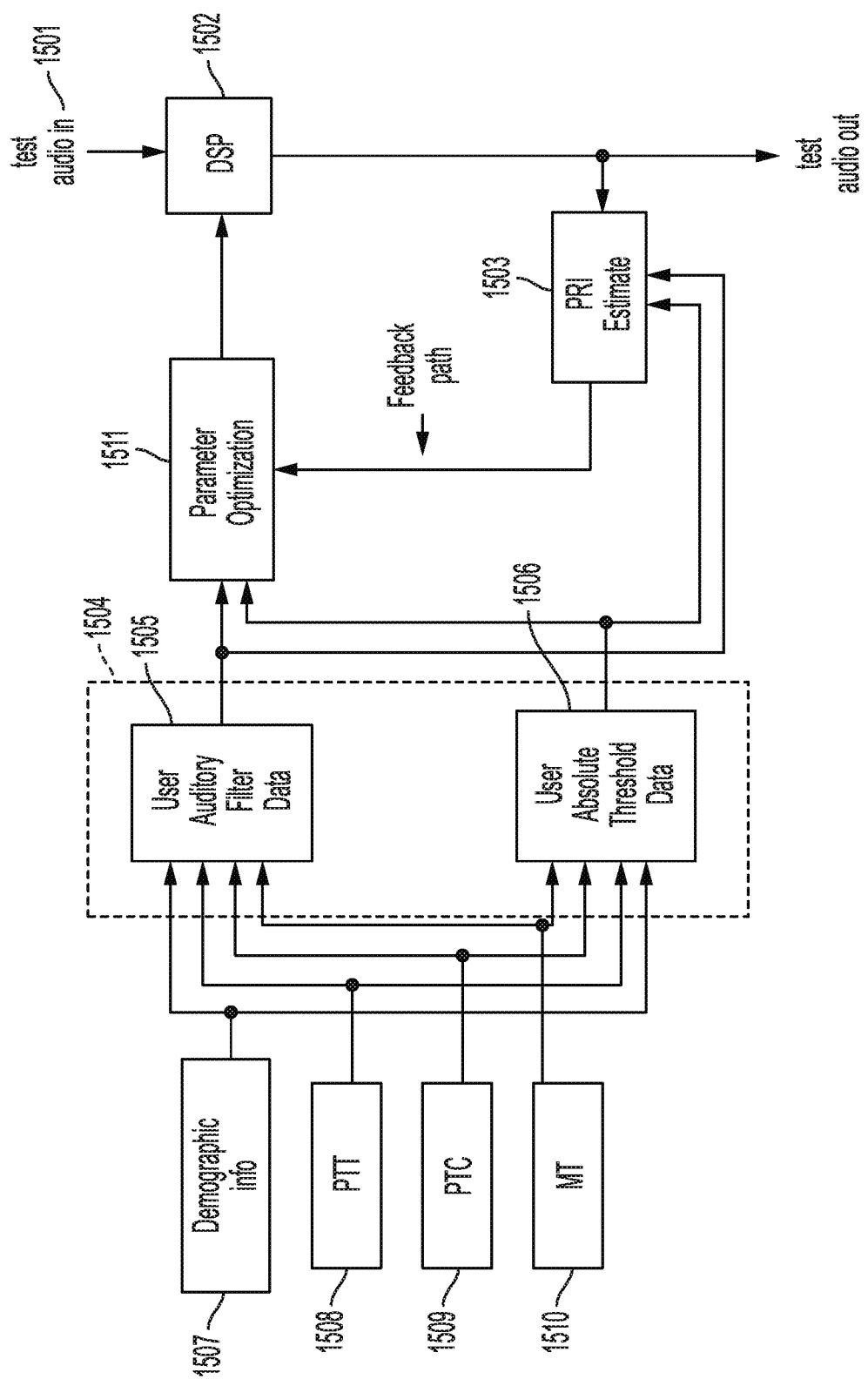
FIG. 15 illustrates a method for attaining DSP parameters from user hearing data through the optimization of perceptually relevant information.

FIGS. 13, 14 and 15 illustrate various exemplary methods of directly calculating parameter sets based on user hearing data according to one or more aspects of the present disclosure. In one embodiment, this may done using a hearing aid gain table prescriptive formulas. In another embodiment, ratio and threshold values for a compressor, as well as gain, in a given multiband dynamic processor signal subband may be calculated by comparing user threshold and suprathreshold information for a listener with that of a normal hearing individual, i.e. reference audiograms and PTC/MT curves. For instance, masking contour curve data, such as PTC or MT, may be used to calculate ratio and threshold parameters for a given frequency subband, while audiogram data may be used to calculate gain within a given frequency subband.

FIGS. 13 and 14 demonstrate one way of configuring the ratio and threshold parameters for a frequency band in a multi-band compression system (see, e.g., commonly owned applications EP18200368.1 and U.S. Ser. No. 16/201,839, the contents of which are herein incorporated by reference). Briefly, a user's masking contour curve is received 1301, a target masking curve is determined 1302, and is subsequently compared with the user masking contour curve 1301 in order to determine and output user-calculated DSP parameter sets 1304.

FIG. 14 combines the visualization of a user masking contour curve 1406 for a listener (listener) and a target masking contour curve 1407 of a probe tone 1450 (with the x-axis 1401 being frequency, and the y-axis 1402 being the sound level in dB SPL or HL) with an input/output graph of a compressor showing the input level 1403 versus the output level 1404 of a sound signal, in decibels relative to full scale (dB FS). The bisecting line in the input/output graph represents a 1:1 (unprocessed) output of the input signal with gain 1.

The parameters of the multi-band compression system in a frequency band are threshold 1411 and gain 1412. These two parameters are determined from the user masking contour curve 1406 for the listener and target masking contour curve 1407. The threshold 1411 and ratio 1412 must satisfy the condition that the signal-to-noise ratio 1421 (SNR) of the user masking contour curve 1406 at a given frequency 1409 is greater than the SNR 1422 of the target masking contour curve 1407 at the same given frequency 1409. Note that the SNR is herein defined as the level of the signal tone compared to the level of the masker noise. The broader the curve will be, the greater the SNR. The given frequency 1409 at which the SNRs 1421 and 1422 are calculated may be arbitrarily chosen, for example, to be beyond a minimum distance from the probe tone frequency 1408.

The sound level 1430 (in dB) of the target masking contour curve 1407 at a given frequency corresponds (see bent arrow 1431 in FIG. 14) to an input sound level 1441 entering the compression system. The objective is that the sound level 1442 outputted by the compression system will match the user masking contour curve 1406, i.e., that this sound level 1442 is substantially equal to the sound level (in dB) of the user masking contour curve 1406 at the given frequency 1409. This condition allows the derivation of the threshold 1411 (which has to be below the input sound level 1441) and the ratio 1412. In other words, input sound level 1441 and output sound level 1442 determine a reference point of the compression curve. As noted above, threshold 1411 must be selected to be lower than input sound level 1441—if it is not, there will be no change, as below the threshold of the compressor, the system is linear). Once the threshold 1411 is selected, the ratio 1412 can be determined from the threshold and the reference point of the compression curve.

In the context of the present invention, a masking contour curve is obtained from a user hearing test. A target masking contour curve 1407 is interpolated from at least the user masking contour curve 1406 and a reference masking contour curve, representing the curve of a normal hearing individual. The target masking contour curve 1407 is preferred over a reference curve because fitting an audio signal to a reference curve is not necessarily optimal. Depending on the initial hearing ability of the listener, fitting the processing according to a reference curve may cause an excess of processing to spoil the quality of the signal. The objective is to process the signal in order to obtain a good balance between an objective benefit and a good sound quality.

The given frequency 1409 is then chosen. It may be chosen arbitrarily, e.g., at a certain distance from the tone frequency 1408. The corresponding sound levels of the listener and target masking contour curves are determined at this given frequency 1409. The value of these sound levels may be determined graphically on the y-axis 1402.

The right panel in FIG. 14 (see the contiguous graph) illustrates a hard knee DRC, with a threshold 1411 and a ratio 1412 as parameters that need to be determined. An input sound signal having a sound level 1430/1441 at a given frequency 1409 enters the compression system (see bent arrow 1431 indicating correspondence between 1430/1441). The sound signal should be processed by the DRC in such a way that the outputted sound level is the sound level of the user masking contour curve 1406 at the given frequency 1409. The threshold 1411 should not exceed the input sound level 1441, otherwise compression will not occur. Multiple sets of threshold and ratio parameters are possible. Preferred sets can be selected depending on a fitting algorithm and/or objective fitting data that have proven to show the most benefit in terms of sound quality. For example, either one of the threshold 1411 and ratio 1412 may be chosen to have a default value, and the respective other one of the parameters can then be determined by imposing the above-described condition.

For calculating gain within a subband signal, the results of an audiogram may be used. For instance, raised thresholds may be compensated for by a corresponding frequency gain.

In one embodiment of the present disclosure, as shown in FIG. 15, DSP parameters in a multiband dynamic processor may be calculated by optimizing perceptually relevant information (e.g. perceptual entropy) through parameterization using user threshold and suprathreshold hearing data (see commonly owned applications U.S. Ser. No. 16/206,376 and EP18208020.0). Briefly, in order to optimally parameterize a multiband dynamic processor through perceptually relevant information, an audio sample 1501, or body of audio samples, is first processed by a parameterized multiband dynamics processor 1502 and the perceptual entropy of the file is calculated 1503 according to user threshold and suprathreshold hearing data 1507. After calculation, the multiband dynamic processor is re-parameterized 1511 according to a given set of parameter heuristics, derived from optimization, and from this—the audio sample(s) is reprocessed 1502 and the PRI calculated 1503. In other words, the multiband dynamics processor is configured to process the audio sample so that it has a higher PRI value for the particular listener, taking into account the individual listener's threshold and suprathreshold information 1507. To this end, parameterization of the multiband dynamics processor is adapted to increase the PRI of the processed audio sample over the unprocessed audio sample. The parameters of the multiband dynamics processor are determined by an optimization process that uses PRI as its optimization criteria.

PRI can be calculated according to a variety of methods found. One such method, also called perceptual entropy, was developed by James D. Johnston at Bell Labs, generally comprising: transforming a sampled window of audio signal into the frequency domain, obtaining masking thresholds using psychoacoustic rules by performing critical band analysis, determining noise-like or tone-like regions of the audio signal, applying thresholding rules for the signal and then accounting for absolute hearing thresholds. Following this, the number of bits required to quantize the spectrum without introducing perceptible quantization error is determined. For instance, Painter & Spanias disclose a formulation for perceptual entropy in units of bits/s, which is closely related to ISO/IEC MPEG-1 psychoacoustic model 2 [Painter & Spanias, Perceptual Coding of Digital Audio, Proc. Of IEEE, Vol. 88, No. 4 (2000); see also generally Moving Picture Expert Group standards https://mpeg.chiariglione.org/standards; both documents included by reference].

Various optimization methods are possible to maximize the PRI of audio samples, depending on the type of the applied audio processing function such as the above mentioned multiband dynamics processor. For example, a subband dynamic compressor may be parameterized by compression threshold, attack time, gain and compression ratio for each subband, and these parameters may be determined by the optimization process. In some cases, the effect of the multiband dynamics processor on the audio signal is non-linear and an appropriate optimization technique such as gradient descend is required. The number of parameters that need to be determined may become large, e.g. if the audio signal is processed in many subbands and a plurality of parameters needs to be determined for each subband. In such cases, it may not be practicable to optimize all parameters simultaneously and a sequential approach for parameter optimization may be applied. Although sequential optimization procedures do not necessarily result in the optimum parameters, the obtained parameter values result in increased PRI over the unprocessed audio sample, thereby improving the listener's listening experience.

Other parameterization processes commonly known in the art may be used to calculate parameters based off user-generated threshold and suprathreshold information. For instance, common prescription techniques for linear and non-linear DSP may be employed. Well known procedures for linear hearing aid algorithms include POGO, NAL, and DSL. See, e.g., H. Dillon, Hearing Aids, $2^{nd}$ Edition, Boomerang Press, 2012.

Fine tuning of any of the above mentioned techniques may be estimated from manual fitting data. For instance, it is common in the art to fit a multiband dynamic processor according to series of tests given to a patient in which parameters are adjusted according to a patient's responses, e.g. a series of A/B tests/decision tree paradigm in which the patient is asked which set of parameters subjectively sounds better. This testing ultimately guides the optimal parameterization of the DSP. In the instance of the present invention, manually-fit DSP parameters results of a given hearing profile can be categorized and inputted into the server database. Subsequently, a user's parameters may be calculated based on the approaches delineated in FIGS. 6 and/or 7.

Figure 16:
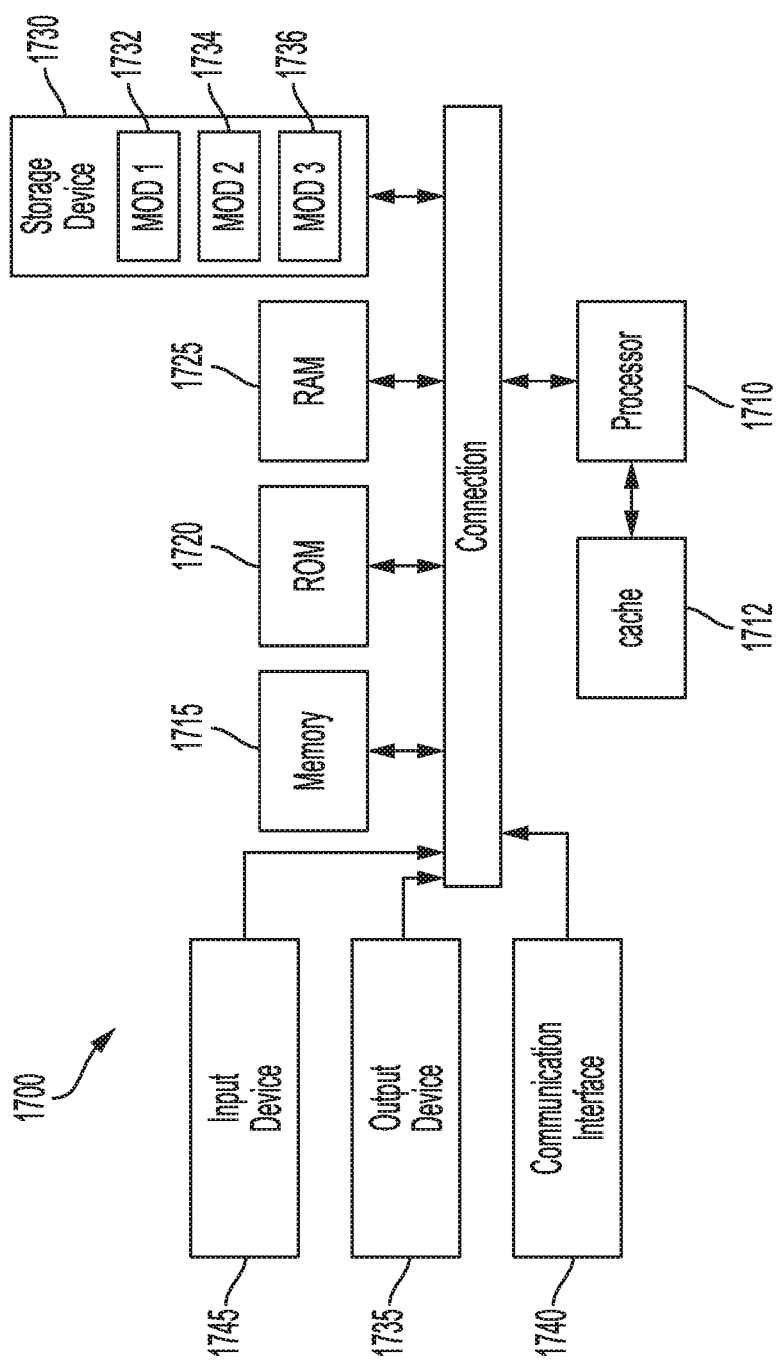
FIG. 16 illustrates an example system embodiment in which one or more aspects of the present disclosure can be employed.

FIG. 16 shows an example of computing system 1600, which can be for example any computing device making up (e.g., mobile device 100, server, etc.) or any component thereof in which the components of the system are in communication with each other using connection 1605. Connection 1605 can be a physical connection via a bus, or a direct connection into processor 1610, such as in a chipset architecture. Connection 1605 can also be a virtual connection, networked connection, or logical connection.

In some embodiments computing system 1600 is a distributed system in which the functions described in this disclosure can be distributed within a datacenter, multiple datacenters, a peer network, etc. In some embodiments, one or more of the described system components represents many such components each performing some or all of the function for which the component is described. In some embodiments, the components can be physical or virtual devices.

Example system 1600 includes at least one processing unit (CPU or processor) 1610 and connection 1605 that couples various system components including system memory 1615, such as read only memory (ROM) 1620 and random access memory (RAM) 1625 to processor 1610. Computing system 1600 can include a cache of high-speed memory 1612 connected directly with, in close proximity to, or integrated as part of processor 1610.

Processor 1610 can include any general purpose processor and a hardware service or software service, such as services 1632, 1634, and 1636 stored in storage device 1630, configured to control processor 1610 as well as a special-purpose processor where software instructions are incorporated into the actual processor design. Processor 1610 may essentially be a completely self-contained computing system, containing multiple cores or processors, a bus, memory controller, cache, etc. A multi-core processor may be symmetric or asymmetric.

To enable user interaction, computing system 1600 includes an input device 1645, which can represent any number of input mechanisms, such as a microphone for speech, a touch-sensitive screen for gesture or graphical input, keyboard, mouse, motion input, speech, etc. Computing system 1600 can also include output device 1635, which can be one or more of a number of output mechanisms known to those of skill in the art. In some instances, multimodal systems can enable a user to provide multiple types of input/output to communicate with computing system 1600. Computing system 1600 can include communications interface 1640, which can generally govern and manage the user input and system output. There is no restriction on operating on any particular hardware arrangement and therefore the basic features here may easily be substituted for improved hardware or firmware arrangements as they are developed.

Storage device 1630 can be a non-volatile memory device and can be a hard disk or other types of computer readable media which can store data that are accessible by a computer, flash memory cards, solid state memory devices, digital versatile disks, cartridges, random access memories (RAMs), read only memory (ROM), and/or some combination of these devices.

The storage device 1630 can include software services, servers, services, etc., that when the code that defines such software is executed by the processor 1610, it causes the system to perform a function. In some embodiments, a hardware service that performs a particular function can include the software component stored in a computer-readable medium in connection with the necessary hardware components, such as processor 1610, connection 1605, output device 1635, etc., to carry out the function.

The presented technology offers an efficient and accurate way to personalize audio replay on a plurality of consumer electronic devices through server-mediated sound personalization. It is to be understood that the present disclosure contemplates numerous variations, options, and alternatives. For clarity of explanation, in some instances the present technology may be presented as including individual functional blocks including functional blocks comprising devices, device components, steps or routines in a method embodied in software, or combinations of hardware and software.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example. The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

The invention claimed is:

1. A method for processing an audio signal, the method comprising:

conducting, using a first instance of an audio personalization application running on a first audio output device, a user hearing test;

outputting, to a server, user hearing data from the user hearing test;

storing the user hearing data on a database associated with the server, wherein the user hearing data is stored using a unique identifier of the user as reference;

determining, based on the user hearing data, a set of calculated digital signal processing (DSP) parameters for a given sound personalization algorithm;

receiving, at the server, a request for personalized auto playback at a second audio output device, the request generated in response to a second instance of the audio personalization application running on the second audio output device receiving a user input comprising the user's unique identifier, wherein the second audio output device is different from the first audio output device;

outputting the calculated DSP parameters to the second instance of the audio personalization application running on the second audio output device, wherein the calculated DSP parameters are outputted by the server in response to receiving the request and the user's unique identifier from the second audio output device; and processing, on the second audio output device, an audio signal by using the given sound personalization algorithm parameterized by the calculated DSP parameters.

2. The method of claim 1, wherein the first audio output device is of a different type than the second audio output device.

3. The method of claim 1, wherein the first instance of the audio personalization application running on the first audio output device and the second instance of the audio personalization application running on the second audio output device are the same.

4. The method of claim 1, wherein determining the set of calculated DSP parameters is performed remote from one or more of the first audio output device and the second audio output device.

5. The method of claim 4, wherein the set of calculated DSP parameters are determined on the server and the server-determined calculated DSP parameters are stored in the database using the unique identifier of the user as reference.

6. The method of claim 1, wherein determining the set of calculated DSP parameters is performed locally on one or more of the first audio output device and the second audio output device.

7. The method of claim 6, wherein the locally determined set of calculated DSP parameters are stored in the database associated with the server, using the unique identifier of the user as reference.

8. The method of claim 1, wherein in response to a user conducting an additional hearing test on any one of a plurality of audio output devices, including the first or second audio output device, the set of calculated DSP parameters is recalculated.

9. The method of claim 8, wherein:
the additional hearing test reflects information from another auditory filter; or
the additional hearing test is a different type of hearing test from a previously conducted hearing test; or
the additional hearing test is a more recent version of a previously conducted hearing test.

10. The method of claim 8, wherein the additional hearing test replaces the hearing data from a previously conducted hearing test with aberrant results.

11. The method of claim 10, wherein a parameter set of the parameterized given sound personalization algorithm comprises at least one of a threshold value of a dynamic range compressor provided in each subband, a ratio value of a dynamic range compressor provided in each subband, and a gain value provided in each subband.

12. The method of claim 10, wherein the given sound personalization algorithm is a multiband dynamics processor.

13. The method of claim 1, wherein the hearing test is one or more of a threshold test, a suprathreshold test, a psychophysical tuning curve test, a masked threshold test, a temporal fine structure test, a speech in noise hearing test and a temporal masking curve test.

14. The method of claim 1, wherein the hearing test measures masking threshold curves within a range of frequencies from 250 Hz to 12 kHz.

15. The method of claim 1, wherein the given sound personalization algorithm operates on subband signals of the audio signal.

16. The method of claim 1, wherein:
the set of calculated DSP parameters is determined using a best fit of the user hearing data with previously inputted hearing data within the server's database; or
the set of calculated DSP parameters is determined using a fitted mathematical function derived from plotted hearing and DSP parameter data; and
the parameters associated with the best fitting and the previously inputted hearing data are selected to correspond to the user's parameters.

17. The method of claim 16, where best fit is determined by one of average Euclidean distance and root mean square difference.

18. The method of claim 1, wherein the audio output device is one of a mobile phone, a tablet, a television, a laptop computer, a hearable device, a smart speaker, a headphone and a speaker system.

19. An audio processing system comprising:
at least one processor; and
at least one memory storing instructions, which when executed cause the at least one processor to perform actions comprising:
conducting, using a first instance of an audio personalization application running on a first audio output device, a user hearing test;
outputting, to a server, user hearing data from the user hearing test;
storing the user hearing data on a database associated with the server, wherein the user hearing data is stored using a unique identifier of the user as reference;
determining, based on the user hearing data, a set of calculated digital signal processing (DSP) parameters for a given sound personalization algorithm;
receiving, at the server, a request for personalized auto playback at a second audio output device, the request generated in response to a second instance of the audio personalization application running on the second audio output device receiving a user input comprising the user's unique identifier, wherein the second audio output device is different from the first audio output device;
outputting the calculated DSP parameters to the second instance of the audio personalization application running on the second audio output device, wherein the calculated DSP parameters are outputted by the server in response to receiving the request and the user's unique identifier from the second audio output device; and
processing, on the second audio output device, an audio signal by using the given sound personalization algorithm parameterized by the calculated DSP parameters.

20. A non-transitory computer-readable storage medium storing a program containing instructions which, when executed on a processor of an audio output device cause the processor to perform actions comprising:
conducting, using a first instance of an audio personalization application running on a first audio output device, a user hearing test;
outputting, to a server, user hearing data from the user hearing test;
storing the user hearing data on a database associated with the server, wherein the user hearing data is stored using a unique identifier of the user as reference;
determining, based on the user hearing data, a set of calculated digital signal processing (DSP) parameters for a given sound personalization algorithm;
receiving, at the server, a request for personalized auto playback at a second audio output device, the request generated in response to a second instance of the audio personalization application running on the second audio output device receiving a user input comprising the user's unique identifier, wherein the second audio output device is different from the first audio output device;

outputting the calculated DSP parameters to the second instance of the audio personalization application running on the second audio output device, wherein the calculated DSP parameters are outputted by the server in response to receiving the request and the user's unique identifier from the second audio output device; and processing, on the second audio output device, an audio signal by using the given sound personalization algorithm parameterized by the calculated DSP parameters.

* * * * *